(12) United States Patent
Hall

(10) Patent No.: US 8,076,158 B2
(45) Date of Patent: Dec. 13, 2011

(54) ENHANCED PROCESS FOR PREPARING CORE SAMPLE THIN SECTIONS

(75) Inventor: Craig Hall, Katy, TX (US)

(73) Assignee: Core Laboratories LP, Houston, TX (US)

( * ) Notice: Subject to any disclaimer, the term of this patent is extended or adjusted under 35 U.S.C. 154(b) by 704 days.

(21) Appl. No.: 12/115,210

(22) Filed: May 5, 2008

(65) Prior Publication Data

US 2009/0272186 A1 Nov. 5, 2009

(51) Int. Cl.
*G01N 1/06* (2006.01)
(52) U.S. Cl. ...................................... 436/174
(58) Field of Classification Search .................. 436/174
See application file for complete search history.

(56) References Cited

U.S. PATENT DOCUMENTS

| | | | |
|---|---|---|---|
| 4,149,803 A | 4/1979 | Litz | |
| 4,868,883 A | 9/1989 | Chen | |
| 4,916,314 A | 4/1990 | Smith | |
| 5,335,293 A | 8/1994 | Vannelli et al. | |
| 5,985,085 A | 11/1999 | Baer et al. | |
| D436,668 S | 1/2001 | Cardy et al. | |
| 6,495,195 B2 | 12/2002 | Baer et al. | |
| 6,887,703 B2 | 5/2005 | Baer et al. | |
| 7,020,307 B2 | 3/2006 | Hinton et al. | |
| 7,075,640 B2 | 7/2006 | Baer et al. | |
| 7,221,447 B2 | 5/2007 | Baer et al. | |

OTHER PUBLICATIONS

Davidson, Michael, "The Quartz Wedge Compensator", Olympus Microscopy Resource Center: Specialized Microscopy Microscopy—Polarized Light Microscopy, Apr. 16, 2007 (Web Archive Retrieval).*
"Thin Sections Tutorial", Mar. 24, 2008 (Web Archive Retrieval).*

* cited by examiner

*Primary Examiner* — Jill Warden
*Assistant Examiner* — Monique Cole
(74) *Attorney, Agent, or Firm* — Mossman, Kumar & Tyler, PC

(57) ABSTRACT

A method of preparing a thin section sample includes affixing the sample to a receptacle using an affixing media that includes a material having a thickness-sensitive characteristic. The sample may then be shaped to have an asymmetric cross-section. The method may further include reducing a thickness of the material until the thickness-sensitive material exhibits a change in an optical characteristic. The added material, which may be quartz, may exhibit a predetermined optical characteristic at a specified thickness and/or exhibit a change in an optical characteristic in response to a change in thickness. In one application, the method may include retrieving the sample from a subterranean formation. For instance, the sample may be retrieved from a gas shale formation.

9 Claims, 1 Drawing Sheet

ENHANCED PROCESS FOR PREPARING CORE SAMPLE THIN SECTIONS

BACKGROUND OF THE DISCLOSURE

None

1. Field of Disclosure

The present disclosure relates to processes and methods for preparing and analyzing core samples retrieved from a subsurface formation.

2. Description of the Related Art

The costs for constructing hydrocarbon producing wells may easily exceed tens of millions of dollars. Therefore, well owners typically seek to characterize a potential hydrocarbon reservoir as accurately as possible before committing funds and other resources to drill a wellbore and construct an oil well to recover oil and gas from such a reservoir. One technique for evaluating subterranean formations involves taking core samples of that formation. The core samples can be evaluated to ascertain the geological make-up of a formation and to predict whether the formation could produce hydrocarbons at a quantity and/or rate that justifies the construction of a oil or gas well.

In aspects, the present disclosure addresses the need for enhanced methods and processes for preparing and analyzing subsurface core samples.

SUMMARY OF THE DISCLOSURE

In aspects, the present disclosure provides a method of preparing a thin section sample. In one embodiment, the method may include adding a material having a thickness-sensitive characteristic to an affixing media; affixing the sample to a receptacle using the affixing media; and shaping the sample to have an asymmetric cross-section. The added material may be formulated or selected to have one or more desired properties. For example, the added material may exhibit a predetermined optical characteristic at a specified thickness. In another example, the added material may exhibit a change in an optical characteristic in response to a change in thickness. In certain applications, the added material may be quartz. The method may further include reducing a thickness of the material until the thickness-sensitive material exhibits a change in an optical characteristic. A variety of geometric shapes may be used to provide the asymmetric cross-section. A wedge shaped-cross-section is one non-limiting example of such a geometric shape. In embodiments, the wedge-shaped cross-section may have a first end having a thickness of approximately thirty microns and a second end having a thickness of less than five microns. In one application, the method may include retrieving the sample from a subterranean formation. For instance, the sample may be retrieved from a gas shale formation.

In aspects, the present disclosure provides a method of analyzing a subterranean formation. One illustrative method may include retrieving a gas shale sample from the subterranean formation; affixing the sample to a slide; varying the thickness of the sample over a cross-section of the sample; and analyzing the sample to determine a parameter of interest. In one application, the method may include affixing a material having a thickness-sensitive characteristic to the slide. One manner of controlling the shaping process includes reducing a thickness of the material until the thickness-sensitive material exhibits a change in an optical characteristic. In certain uses, varying the thickness may result in a cross-section wherein a first end of the sample has a thickness greater than a thickness of a second end of the sample. For instance, the first end may have a thickness of approximately thirty microns and the second end has a thickness of less than five microns.

In aspects, the present disclosure provides a gas shale thin section that may be examined at a laboratory. An illustrative gas shale thin section may include a slide; a gas shale sample having an asymmetric thickness across a cross-section; and an affixing media securing the sample to the slide. The affixing media may include a material having a thickness-sensitive characteristic. The included material may exhibit a predetermined optical characteristic at a specified thickness. The material, which may be quartz, may also exhibit a change in an optical characteristic in response to a change in thickness. As noted previously, the cross-section may be a wedge-shaped cross-section.

The above-recited examples of features of the disclosure have been summarized rather broadly in order that the detailed description thereof that follows may be better understood, and in order that the contributions to the art may be appreciated. There are, of course, additional features of the disclosure that will be described hereinafter and which will form the subject of the claims appended hereto.

BRIEF DESCRIPTION OF THE DRAWINGS

For detailed understanding of the present disclosure, references should be made to the following detailed description of the preferred embodiment, taken in conjunction with the accompanying drawings, in which like elements have been given like numerals and wherein.

DETAILED DESCRIPTION OF THE DISCLOSURE

Figure 1:
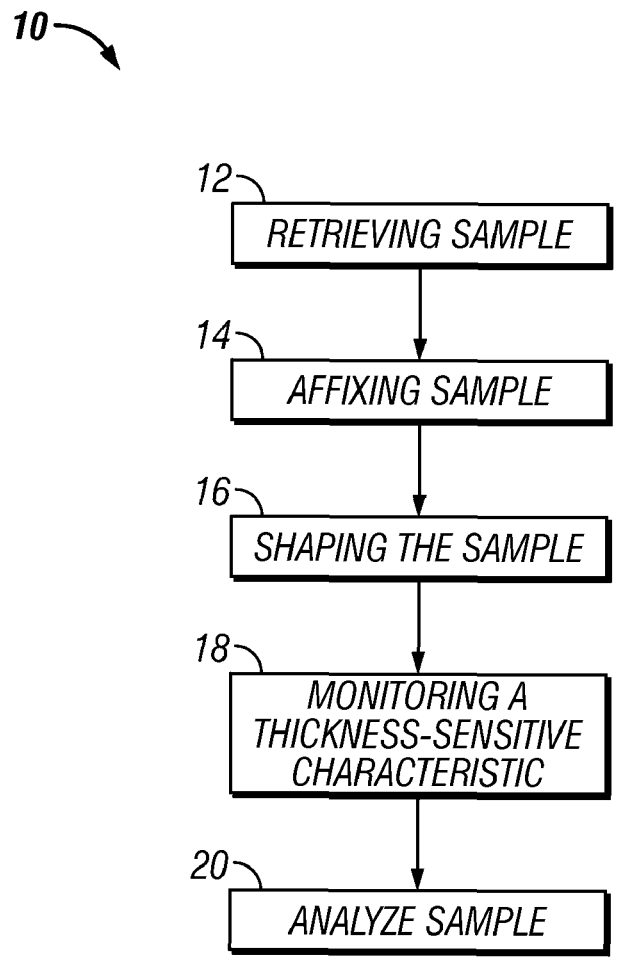
FIG. 1 is a flow chart of one illustrative process in accordance with the present disclosure.

As will become apparent below, the present disclosure provides for enhanced analysis of samples retrieved from subterranean formations. The present disclosure is susceptible to embodiments of different forms. There are shown in the drawings, and herein will be described in detail, specific embodiments of the present disclosure with the understanding that the present disclosure is to be considered an exemplification of the principles of the disclosure, and is not intended to limit the disclosure to that illustrated and described herein. Further, while embodiments may be described as a system made up of several components or as a combination of two or more features, it should be understood that the individual components or individual features may themselves represent advancements over the prior art and may be separately utilized for any given system or combination.

Referring now to FIG. 1, there is shown one illustrative process 10 that may be used to prepare thin section sample that may be evaluated or analyzed to characterize a subterranean formation of interest. At step 12, a sample, such as a core sample, may be recovered from the subterranean formation. This retrieval may be performed by using a coring tool or other device that is conveyed into a borehole intersecting the subterranean formation. Such coring tools may be conveyed via wireline, drill pipe or coiled tubing. Upon being retrieved to the surface, the sample may be preserved and transported to a suitable facility for further processing and analysis. In embodiments, the sample may be a gas shale sample that may be useful in evaluating a lithological, geophysical, petrophysical, or other characteristic of the formation.

To prepare the sample for analysis, the sample may be affixed to a receptacle using an affixing media at step 14. The affixing media may be an epoxy or other material that connects or affixes the sample to a suitable receptacle. The affixing media may be formulated to include a material having a thickness-sensitive characteristic. As used herein, the term "thickness-sensitive characteristic" refers to a predetermined characteristic that is exhibited at a given thickness. For example, the material may exhibit a known optical characteristic at a specific thickness. Moreover, the material may exhibit different characteristics at different specific thicknesses. In still other variants, a parameter, such as a magnitude or intensity, of a given characteristic may increase or decrease. That is, the material may exhibit a change in a characteristic or a change in a parameter of the characteristic in response to a change in thickness. Therefore, by monitoring or measuring the predetermined characteristic, the thickness of the material may be estimated.

One non-limiting example of a material that has such a characteristic is quartz, which has optical characteristics that are related to thickness of a grain. At thicknesses above approximately thirty microns, quartz grain may be yellowish. At thicknesses of approximately thirty microns, quartz grain may exhibit a grayish color. In addition to optical characteristics, other characteristics may include a change in an electrical property or a mechanical property.

At step 16, the core sample may be shaped to facilitate analysis. By shaping, it is generally meant to form the core sample to have a defined geometric configuration and to have one or more predetermined dimensions. The shaping may be performed by mechanically working the core sample using devices such as high-precision grinders. However, other devices may also be used to provide the core sample with a suitable configuration.

In many applications, certain characteristics of interest relating to a formation become observable when the core sample has a certain thickness (e.g., thirty microns, fifteen microns, etc.). Thus, it may be desirable to reduce the thickness of the sample to enable the observation or quantification of such characteristics. Advantageously, the shaping step 16 may be controlled by using the material having the thickness-sensitive property.

At step 18, the thickness-sensitive characteristic may be monitored or observed to determine whether a sample or a portion of the sample has reached a target thickness during the shaping step 16. For example, both the thickness-sensitive material and the sample may be reduced in thickness at the same time and in the same manner. For instance, it may be desired to reduce an end of a sample to thirty microns. In that situation, one end of the sample, together with the quartz grains at that end, may be gradually ground down to reduce their thicknesses. Grinding may be halted once the quartz grains exhibit a particular color (e.g., a gray color), which indicates that the quartz and the adjacent sample end are at an approximately thirty micron thickness.

In embodiments, the sample may be further shaped to provide a varied or asymmetric thickness across a cross-section of the sample. For instance, one end of the sample may have a thickness of thirty microns and the other end of the sample may have a thickness of less than five microns. Such a cross-section may be described as a wedge-shaped cross-section. The change in thickness across the cross-section may allow properties or characteristics of the sample to be more effectively analyzed. For example, properties that become observable or quantifiable at thicknesses less than thirty microns may be more readily discernable in the region between the two ends of the sample. Also, it should be appreciated that the gradient of the reduction in thickness may be controlled such that the thickness of a point or location along the cross-section may be readily estimated.

After the sample has been prepared, the sample may be analyzed at step 20. In embodiments, the sample may be fixed to a glass microscopic slide and examined using a microscope. In other embodiments the sample may be fixed to a receptacle that allows a digital imaging of the sample. That is, the sample may be analyzed manually or through the use of machines.

Figure 2:
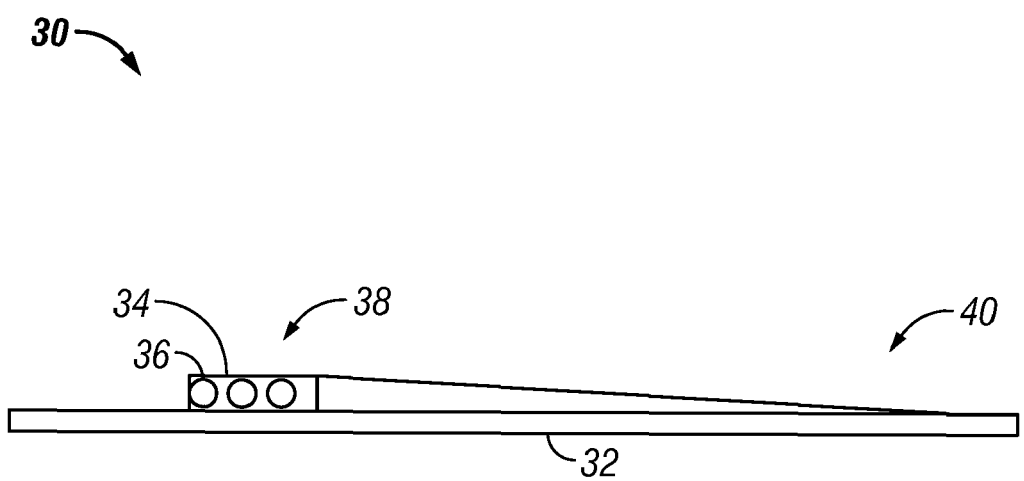
FIG. 2 is a schematic sectional view of a thin section sample prepared using the FIG. 1 embodiment.

Referring now to FIG. 2, there is shown a cross-section of one embodiment of a thin section sample 30 that has been prepared using the FIG. 1 process. The sample 30 may be fixed on a receptacle 32 with an affixing media 34 that includes a material 36 that has a thickness-sensitive characteristic. In other embodiments, the material 36 may be separate from the affixing media 34. The affixing media 34 may be an epoxy or other material that binds the sample 30 to the receptacle 32. The receptacle 32 may be a glass microscopic slide.

In one embodiment, the thin section sample 30 may be a gas shale sample, which may not have a native material that has a thickness-sensitive characteristic, such as quartz. While quartz grain may be suitable for many applications, other material, which may or may not be granular, may also be utilized for the material 36.

As shown, the cross-section of the sample 30 is asymmetric, i.e., it has a wedge shaped-cross-section. The wedge-shaped cross-section has a first end 38 that has a thickness that is greater than a thickness of a second end 40. For example, the material 36 and the first end 38 may have a thickness of thirty microns. The second end 40 may have a cross-section of less than five microns. Advantageously, the sample 30, thanks to the variation in thicknesses, allows properties that become measurable or observable at some thickness between thirty and zero microns to become discernable. Of course, other shapes for cross-sections may also be utilized.

From the above, it should be appreciated that one illustrative method of preparing a thin section sample includes adding a material having a thickness-sensitive characteristic to an affixing media; affixing the sample to a receptacle using the affixing media; and shaping the sample to have an asymmetric cross-section. The added material may be formulated or selected to have one or more desired properties or features that may assist during the shaping step. For example, the added material may exhibit a predetermined optical characteristic at a specified thickness and/or exhibit a change in an optical characteristic in response to a change in thickness. In certain applications, the added material may be quartz. One method of controlling the shaping of the sample includes reducing a thickness of the material until the thickness-sensitive material exhibits a change in an optical characteristic. Such an change may indicate that a specified thickness has been reached. A variety of geometric shapes may be used to provide the asymmetric cross-section; a wedge shaped-cross-section being one non-limiting example. In embodiments, the wedge-shaped cross-section may have a first end having a thickness of approximately thirty microns and a second end having a thickness of less than five microns.

From the above, it should be appreciated that the present disclosure also provides a method of analyzing a subterranean formation that in one illustrative application includes retrieving a gas shale sample from the subterranean formation; affixing the sample to a slide; varying the thickness of the sample over a cross-section of the sample; and analyzing the sample to determine a parameter of interest.

From the above, it should further be appreciated that the present disclosure provides a gas shale thin section that enables enhanced analysis of subterranean gas shale formations. One illustrative gas shale thin section may be a gas shale sample having an asymmetric cross-sectional thickness and that is affixed to a slide with an affixing media that includes a material having a thickness-sensitive characteristic.

The foregoing description is directed to particular embodiments of the present disclosure for the purpose of illustration and explanation. It will be apparent, however, to one skilled in the art that many modifications and changes to the embodiment set forth above are possible without departing from the scope of the disclosure. Thus, it is intended that the following claims be interpreted to embrace all such modifications and changes.

What is claimed is:

1. A method of preparing a thin section sample, comprising:
   (a) adding a material having a thickness-sensitive characteristic to an affixing media;
   (b) affixing the sample to a receptacle using the affixing media; and
   (c) shaping the sample to have an asymmetric cross-section.

2. The method of claim 1, wherein the material exhibits a predetermined optical characteristic at a specified thickness.

3. The method of claim 1, wherein the material exhibits a change in an optical characteristic in response to a change in thickness.

4. The method of claim 1, wherein the material is quartz.

5. The method of claim 1, further comprising reducing a thickness of the material until the thickness-sensitive material exhibits a change in an optical characteristic.

6. The method of claim 1, wherein the asymmetric cross-section is a wedge shaped-cross-section.

7. The method of claim 6, wherein the wedge-shaped cross-section has a first end having a thickness of approximately thirty microns and a second end having a thickness of less than five microns.

8. The method of claim 1, further comprising retrieving the sample from a subterranean formation.

9. The method of claim 8, wherein the sample is from a gas shale formation.

* * * * *